United States Patent [19]

Büchel

[11] Patent Number: 5,024,615

[45] Date of Patent: Jun. 18, 1991

[54] SURGICAL ASPIRATION DEVICE

[75] Inventor: Udo P. Büchel, Billdal, Sweden

[73] Assignee: Astra Meditec Aktiebocag, Molndal, Sweden

[21] Appl. No.: 456,045

[22] PCT Filed: Nov. 24, 1981

[86] PCT No.: PCT/SE81/00341

§ 371 Date: Jul. 19, 1982

§ 102(e) Date: Jul. 19, 1982

[87] PCT Pub. No.: WO82/01824

PCT Pub. Date: Jun. 10, 1982

Related U.S. Application Data

[63] Continuation of Ser. No. 185,244, Apr. 19, 1988, abandoned, which is a continuation of Ser. No. 943,847, Dec. 24, 1986, abandoned, which is a continuation of Ser. No. 649,971, Sep. 12, 1984, abandoned, which is a continuation of Ser. No. 403,642, filed as PCT SE81/00341 on Nov. 24, 1981, published as WO82/01824 on Jan. 10, 1982, abandoned.

[30] Foreign Application Priority Data

Dec. 4, 1980 [SE] Sweden .................. 8008525

[51] Int. Cl.$^5$ .................................. A61M 1/00
[52] U.S. Cl. ...................... 604/119; 604/45; 604/902; 433/95
[58] Field of Search ............... 604/43, 45, 118, 119, 604/902; 433/91, 95, 100

[56] References Cited

U.S. PATENT DOCUMENTS

| | | | |
|---|---|---|---|
| 1,188,180 | 6/1916 | Kells ........................ | 604/45 |
| 1,388,312 | 8/1921 | Seeger ....................... | 433/96 |
| 1,889,425 | 11/1932 | Sorensen ..................... | 604/35 |
| 3,469,582 | 9/1969 | Jackson ...................... | 604/119 |
| 3,528,427 | 9/1970 | Sheridan ..................... | 604/45 |
| 3,610,226 | 10/1971 | Albisser ..................... | 604/27 |
| 4,031,896 | 6/1977 | Runnmark ..................... | 604/119 |
| 4,068,664 | 1/1978 | Sharp et al. ................. | 433/91 |
| 4,334,538 | 6/1982 | Juhn ......................... | 604/119 |
| 4,382,442 | 5/1983 | Jones ........................ | 604/28 |
| 4,400,168 | 8/1983 | Buechel et al. ............... | 604/48 |

FOREIGN PATENT DOCUMENTS

| | | |
|---|---|---|
| 612074 | 10/1932 | Fed. Rep. of Germany . |
| 2414578 | 10/1974 | Fed. Rep. of Germany . |
| 2285148 | 4/1976 | France . |
| 2287918 | 5/1976 | France . |
| 2294680 | 7/1976 | France . |
| 350404 | 7/1937 | Italy ................ 604/93 |
| 140617 | 7/1979 | Norway . |
| 87676 | 10/1936 | Sweden . |
| 7413157 | 7/1976 | Sweden . |

Primary Examiner—Randall L. Green
Assistant Examiner—Randy Shay
Attorney, Agent, or Firm—White & Case

[57] ABSTRACT

Surgical aspiration device for use in surgical operations, whereby the aspiration device is intended for use in atraumatic aspiration, tissue aspiration and disection. The surgical aspiration device comprises a handle with an inner tube and an outer tube which extend from the handle and which are arranged concentrically, with an interstice formed between them. Adjacent to the handle is an inlet opening which allows air into said interstice. When a vacuum is applied to the inner tube for aspiration, air passes into the interstice and into the inner tube, whereby the aspirated liquid column is broken and atraumatic aspiration can take place.

4 Claims, 1 Drawing Sheet

SURGICAL ASPIRATION DEVICE

This application is a continuation of application Ser. No. 185,244, filed on Apr. 19, 1988 now abandoned; which is a continuation of application Ser. No. 943,847, filed Dec. 24, 1986 now abandoned; which is a continuation of application Ser. No. 649,971, filed Sept. 12, 1984 now abandoned; which is a continuation of application Ser. No. 403,642, filed as PCT SE81/00341 on Nov. 24, 1981, published as WO82/01824 on Jun. 10, 1982, now abandoned.

TECHNICAL FIELD

The present invention is related to a surgical aspiration device, which is intended for use in surgical operations for removing blood, other liquids and/or matter from the operation area.

The object of the present invention is to obtain a surgical aspiration or suction device by which blood, wound secret and solid matter can be removed during an operation, whereby aspiration can be done either in an atraumatic manner or for dissection and suction of tissues.

BACKGROUND OF THE INVENTION

From Swedish Patent No. 7413157-4 (publ. no. 383959) a surgical suction device is previously known, which comprises a point aspirator and an outer aspiration tube arranged round the point aspirator, whereby the outer tube is axially displaceable in order to enable point aspiration or sump aspiration. The suction device is produced to enable alternative point or sump aspiration, i.e., aspiration in a limited area, or aspiration for removal of larger amounts of liquid from a greater area. This aspiration cannot be made to work twice in an atraumatic manner, and on aspiration tissue will be invaginated by suction adheration.

Use of the aspiration technique in surgical operations generally requires the establishment of an air pressure lower than the ambient pressure at a certain spot and thereby the achievement of a flow of air, liquid, tissue parts or other matter in a desired direction. The principle implies the establishment of a reduced pressure in a tube or a mouthpiece attached thereto, which is directed to the spot where aspiration is to take place. In a free open mouthpiece connected to a vacuum source a balance is rapidly established between flow rate and vacuum level.

On aspiration of a liquid however, a column of liquid will be built up, as air does not continuously reach the mouthpiece. The rapid movement of the liquid column in the tube causes a piston movement which by its force makes tissue adhere by suction and invaginate into the mouthpiece. Suction adheration frequently causes a trauma in the tissue, which trauma can be more or less serious depending on where it occurs, and which in any event is a damage to organs and body, which must be healed. Further, suction adheration means that the work in the wound area is impeded as the operator must eliminate the adheration with a special manipulation and force.

SUMMARY OF THE INVENTION

The above mentioned problems have now unexpectedly become capable of solution by the present invention, whereby the liquid column mentioned may be broken and suction adheration is counteracted. The invention relates to a surgical aspiration device comprising a tubular handle, which at one end thereof has an outlet for connection to a vacuum source, and which at the other end thereof has a projecting point aspirator shaped as a tube which at least at its front end is provided with an axially (frontally) arranged aspiration opening. The invention is characterized in that the handle further is provided with an outer tube arranged substantially concentically with the point aspirator, which outer tube extends along the entire point aspirator and which has an opening at its front end adjacent to the front end of the point aspirator, whereby an interstice is arranged between the outer tube and the point aspirator, and whereby the outer tube has an air inlet opening adjacent to the handle, through which opening air is allowed to pass along the outside of the point aspirator to the aspiration opening thereof.

An embodiment of the invention is characterized in that the outer tube extends further beyond the front end of the point aspirator.

A further embodiment of the invention is characterized in that the point aspirator is arranged without any joint to the outer tube at its front end.

A still further embodiment of the invention is characterized in that the outer tube and the point aspirator are joined to each other at the front ends thereof, whereby the point aspirator has at least one laterally arranged opening adjacent to the front end thereof, for connection between the interior of the point aspirator and the interstice.

A further preferred embodiment of the invention is characterized in that the point aspirator at its front end has at least one further laterally arranged opening connecting the interior of the point aspirator with the interstice.

Another preferred embodiment of the invention is characterized in that the outer tube is held axially displaceable in relation to the handle.

A further embodiment of the invention is characterized in that the ratio between the cross-sectional area of the point aspirator and the cross-sectional area of the interstice at the front end is 1:1–1.4.

Another further embodiment of the invention is characterized in that the diameter of the air inlet opening is substantially equal to the outer diameter of the point aspirator.

By the present invention is achieved a continuous flow of air during aspiration, in the direction opposite to the flow of liquid, on the outside of the point aspirator to the tip of the mouthpiece, where the air breaks the liquid column that would otherwise be formed. The air in the aspiration device and the aspiration tube connected there to expands at an increased vacuum in the tube, in contrary to the liquid, and thus counterbalances the increased suction force. Through its construction the aspiration device can be used with a maximal vacuum, as produced by the central vacuum installations in hospitals.

BRIEF DESCRIPTION OF THE DRAWINGS

The invention will be described further with reference to the accompanying drawings of preferred embodiments of the invention, wherein.

Figure 1:
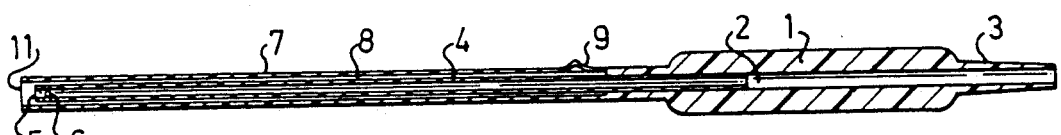
FIG. 1 shows an aspiration device according to the invention in section along its length axis.

DESCRIPTION OF EXEMPLARY EMBODIMENTS 1 denotes a substantially cylindrical handle having a longitudinal bore 2. The handle is at one end thereof provided with a connection means 3 for connection to a tube (not shown) for further connection to a vacuum source (not shown). The handle 1 is at its other, front end provided with a point aspirator 4 shaped as a tube which extends forwardly to a suitable distance from the handle. The aspiration device may be made of plastic material or glass. A plastic material is preferred when the device is to be disposed of after use once. The point aspirator 4 is open at its front end 5 but is also suitably provided with a number of openings 6 arranged laterally near the orifice 5 of the tube. Further, an outer tube 7 is arranged at the front end of the handle concentrically around the point aspirator 4 in such a manner that an interstice 8 is present between the inside of the outer tube 7 and the outside of the inner tube 4. Further, the outer tube 7 is provided with a laterally arranged air inlet opening 9 adjacent to the front end of the handle 1, which opening 9 connects the interstice with the exterior.

The outer tube is imperforate throughout its extent except for the inlet opening so that ambient air can enter it only through the inlet opening.

Figure 2:
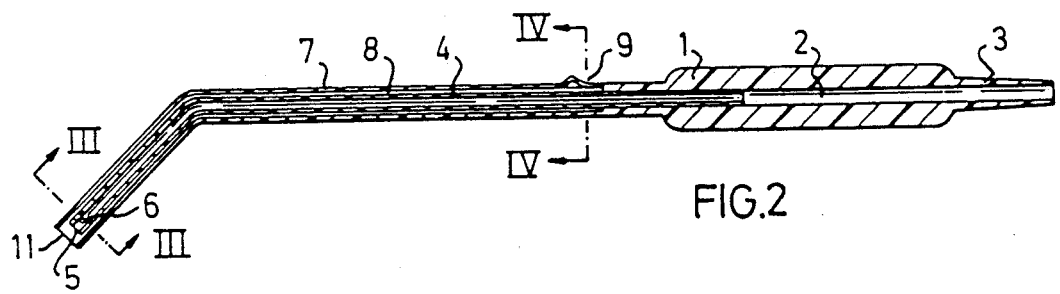
FIG. 2 is a section in accordance with FIG. 1 of a bent aspiration device according to one embodiment of the invention.

Suitably, the opening 9 in the tube can be shaped as shown so as to anatomically fit with a finger tip for hand control of the size of the opening 9, i.e., the degree of connection between the interstice and the exterior in this part. The outer tube 7 should also extend beyond the inner tube 4 in the manner shown in FIGS. 1 and 2 to ensure breaking of the liquid column. The outer tube shall thus extend 1-5 mm forwardly beyond the inner tube 4, whereby the tip of the inner tube is to be placed at a distance backwards in the outer tube 7 equal to the outer diameter of the inner tube 4. The outer tube 7 here has a frontal opening 11.

The ratio between the cross-sectional area of the inner tube and at the tip thereof and the cross-sectional area of the air space between the outside of the inner tube 4 and the inside of the outer tube 7 should be $$\left( \frac{C^2 \times \pi}{4} - \frac{B^2 \times \pi}{4} \right) : \frac{A^2 \times \pi}{4} \approx 1:1.2$$

wherein
A is the inner diameter of the inner tube;
B is the outer diameter of the inner tube; and
C is the inner diameter of the outer tube.

Further, the diameter of the air inlet opening 9 should be equal to the outer diameter of the inner tube and should be placed as far back towards the handle as possible.

Figure 5:
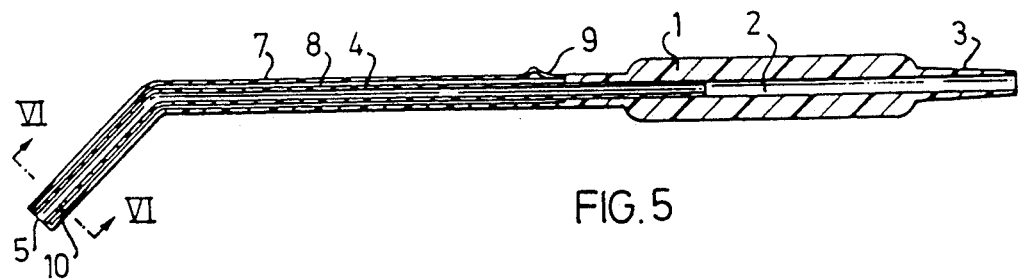
FIG. 5 shows a further embodiment in accordance with FIG. 1.
Figure 3:
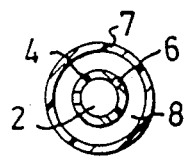
FIG. 3 shows the section III—III in FIG. 2.
Figure 4:
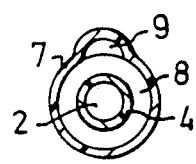
FIG. 4 shows the section IV—IV in FIG. 2.
Figure 6:
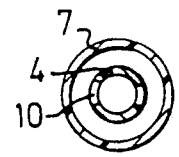
FIG. 6 shows the section VI—VI in FIG. 5.

FIG. 5 shows another preferred embodiment of the aspiration device according to the present invention, whereby the inner tube 4 is extended and joined with the outer tube 7. The inner tube has thereby been provided with a number of side openings 10, suitably three, by which the aspirated air can pass into the inner tube 4 on use of the aspiration device. The front end of the aspiration device can then be shaped as shown in FIG. 5 with a rounded tip prepared by bending in and joining the outer tube 7 with the inner tube 4, or by narrowing and joining the outer tube 7 with the inner tube 4. The side openings 10 are then placed as far forwardly as possible without impeding free passage of air from the air space/interstice between the inner tube 4 and the outer tube 7. The added area of the side openings should not be less than the cross-sectional area of the inner tube 4.

The outer tube 7 can also be held axially displaceable in relation to the handle 1, whereby the position of the outer tube 7 relative to the point aspirator, i.e., the inner tube 4, can be varied, thereby varying the amount of air aspirated at the tip of the point aspirator. The air inlet opening also may be covered more or less, whereby the amount of air flowing through the interstice 8 may be varied.

In use of the aspiration device according to the invention it is connected at its connection means 3 to a tube connected to a vacuum source, such as a central surgical aspiration source or the like. The aspiration device is then lowered into the operation area at a surgical incision on a patient. The operator can now, depending on the amount of liquid or matter to be removed, elect to close or not close the air inlet opening 9 with a finger tip. If large amounts of liquid are to be radically drained the opening 9 is closed whereby maximal suction effect is obtained, while in case of risk of invagination of sensitive tissue parts the operator holds the opening 9 open so that air may always break the liquid column aspirated through the tip, i.e. the negative pressure at the tip is reduced so as to prevent harmful invagination. The amount of air let in through the opening 9 can also easily be adapted to the conditions by covering said opening more or less with a finger tip.

I claim:

1. A surgical aspiration device comprising a tubular handle having a first end with an outlet for connection with a vacuum source and a second end, the second end being connected to a projecting point aspirator tube and supporting the aspirator tube for connection to the vacuum source, the aspirator tube being connected at a proximal terminus thereof to the handle and having a distal terminus open for point aspiration, an air supply tube extending along the aspirator tube, the air supply tube being in fluid communication with the aspirator tube through an interconnecting opening near the distal terminus of the aspirator tube, an inlet opening to atmosphere in the air supply tube near said handle, the air supply tube being imperforate throughout its extent except for the inlet opening so that ambient air can enter it only through the inlet opening, said inlet opening in the air supply tube being located to facilitate hand control and stoppage of the flow of air therethrough by a finger of the user during use of the aspirator device, whereby aspiration at a point is controlled by the user variably and selectively opening and closing the inlet opening to vary and stop selectively the air flow through the air supply tube to the aspirator tube via the interconnecting opening and thereby controllably vary the vacuum at the open distal terminus of the aspirator tube where point aspiration occurs.

2. The aspiration device of claim 1 wherein the air supply tube is in surrounding relation to the aspirator tube along substantially the entire length thereof to form an interstitial passage between the interior of the air supply tube and the exterior of the aspirator tube for flow of air to the interconnecting opening.

3. A surgical aspiration device according to claim 2, wherein the ratio between the cross-sectional area of said aspirator and the cross-sectional area of said interstitial opening at said distal end is between 1:1 and 1:1.4.

4. A surgical aspiration device according to claim 1, wherein the diameter of said air inlet opening is substantially equal to the outer diameter of said point aspirator.

* * * * *